United States Patent [19]

Nehring

[11] 4,191,204

[45] Mar. 4, 1980

[54] PRESSURE RESPONSIVE FLUID COLLECTION SYSTEM

[75] Inventor: John R. Nehring, Bergen, N.J.

[73] Assignee: International Paper Company, New York, N.Y.

[21] Appl. No.: 567,552

[22] Filed: Apr. 14, 1975

[51] Int. Cl.² ............................................. A61M 1/00
[52] U.S. Cl. ...................................... 137/205; 138/45
[58] Field of Search .......................... 137/205; 138/45; 141/59

[56] References Cited

U.S. PATENT DOCUMENTS

| 1,483,596 | 2/1924 | Remington | 137/205 |
| 2,454,929 | 11/1948 | Kempton | 138/45 |
| 2,781,058 | 2/1957 | Warhus | 138/45 |
| 3,863,663 | 2/1975 | Bornhorst | 137/205 |
| 3,915,189 | 10/1975 | Holbrook | 137/205 |

FOREIGN PATENT DOCUMENTS 559469 3/1957 Italy .......................................... 138/45

Primary Examiner—Alan Cohan
Attorney, Agent, or Firm—Finnegan, Henderson, Farabow, Garrett & Dunner

[57] ABSTRACT

A collection system having a vacuum source in flow communication with a closed fluid collection vessel which is in flow communication with an inlet conduit disposed to apply the vacuum to non-gaseous fluids. The non-gaseous fluids to be collected are ingested through the inlet conduit through an inlet port to the closed collection vessel where they are retained. The collection vessel is kept at a negative gauge pressure through an outlet port connecting the collection vessel to the vacuum source. A variable restriction means is provided at one point between the outlet port and the vacuum source for reducing the cross-sectional area available for flow. The restriction means is responsive to the pressure differential across it and thus tends to reduce gas flow through the system in response to increasing differential pressure.

13 Claims, 13 Drawing Figures

PRESSURE RESPONSIVE FLUID COLLECTION SYSTEM

BACKGROUND OF THE INVENTION

The present invention relates to material collection systems using gas flow induced by a vacuum source to convey non-gaseous material to be collected.

More particularly the invention relates to collection systems particularly adapted to suctioning of body fluids by creating a negative gauge pressure in a collection vessel and ingesting non-gaseous fluid through a conduit in flow communication with the vessel.

In a typical hospital, several operating rooms have body fluid collection systems connected to the same central vacuum source. When prior art systems expose an inlet conduit to the atmosphere, they unnecessarily consume additional energy in driving the pump section of the vacuum source by ingesting large quantities of air. The pumping of such large quantities of air through the prior art systems is, in addition to being wasteful of energy, excessively noisy. Also, the level of vacum may become dangerously low.

The present invention reduces the flow of gas through the system upon exposure of an inlet conduit to the atmosphere and thus reduces energy usage and noise. This can be accomplished while maintaining the vacuum level at a desirable level in systems including a plurality of inlet conduits, without compromising the maximum attainable vacuum developed by such a system and without significant reductions in the final rate of collection of non-gaseous fluids.

The present invention is particularly well suited for use in medical applications where the non-gaseous fluids to be collected are body fluids generated by surgical and non surgical intrusion into the body. In such medical applications, the collection system should initially exert gentle suction on the fluids available for collection the body which thereby minimizes grabing of adjacent tissue or lung collapse. The system should, however, provide sufficient differential pressure between the collection vessel and the inlet conduit so that relatively viscous materials can be ingested into the inlet conduit tip and subsequently as the vacuum increases into the collection vessel.

A prior art system is described in U.S. Pat. No. 3,812,855 where an ophthalmic surgical device is disclosed having fluid dispensing and collection means. The device of this reference uses a variable flow restricting element to control the flow rate of fluid either delivered or ingested by a surgical probe. The extraction or delivery of fluid to the interior of the eye is, of course, a critical manipulation of material and the variation of fluid amounts and their flow rates of extraction and insertion must be varied exactly. This prior art reference controls the flow rate of fluid by acting on the fluid itself. By contrast the present invention controls the rate of extraction of fluids utilizing a differential pressure responsive restriction at one point within the vacuum line of a collection system. No attempt is made at precise control or variation of the rate of fluid collection as taught by the cited reference. The present invention does not contemplate the control of the rate of delivery of a fluid to the body.

U.S. Pat. No. 3,763,862 discloses a vacuum collection system particularly applicable to multi-station dental apparatus. This reference discloses a displaceable diaphragm disposed to close the inlet upon manual movement of a control valve. The reference also discloses a valve in the inlet portion of the apparatus whereby the vacuum applied for collection is controlled by opening the inlet system through the valve to the atmosphere. In this reference the responsive diaphragm is in the inlet portion of the device, is responsive only to the position of a manually-controlled valve and acts solely as an on-off valve. The valve effecting the vacuum within the system is in the inlet portion of the system and merely degrades the vacuum by venting the inlet to the atmosphere.

U.S. Pat. Nos. 3,848,628 and 3,814,098 both disclose a fluid collection device comprising a flexible bag within a rigid container. Vacuum is applied to both sides of the flexible bag within the container to prevent its collapse due to differential pressures. There are provided slits in the bag that allow gas flow through the bag to aid the pressure equalization. In both references, the size of the orifices are determined by the gas flow rate which is in turn determined by the degree of vacuum applied to the system. Where the vacuum is high, the orifices enlarge to accommodate the larger gas flow through the system.

The size of the orifices of these cited references increase in cross section upon the application of increasing differential pressures.

The invention as disclosed in the illustrative embodiments herein provides an improved means of collecting non-gaseous fluids. By reducing the flow rate of gas through the system in response to increases in differential pressures across a variable flow restriction the invention desirably provides an increased rate of vacuum buildup when the inlet is partially or fully blocked while reducing the amount of gas ingested when the inlet is exposed to the atmosphere. In addition, the invention reduces the rate of exhaustion of gases from a cavity from which the non-gaseous fluid is being collected. In medical applications, the invention avoids air exhaustion from the lungs during trachea suctioning and minimizes tissue grab adjacent the inlet.

SUMMARY OF THE INVENTION

The collection system of this invention comprises a vacuum source, a closed fluid collecton vessel having an inlet port and an outlet port, an inlet conduit having its discharge end in flow communication with the inlet port and a vacuum conduit connecting the vacuum source and the outlet port. The vacuum conduit and the outlet port form a vacuum line. A flow restricting means reduces the cross-sectional area of the vacuum line available for flow at one point in the vacuum line in inverse proportion to increases in the differential pressure across the flow restricting means. That is, as the differential pressure across the flow restricting means increases, the area available for flow decreases.

In a preferred embodiment of the invention an orifice is provided within the vacuum line in an elastically deformable member, and increases in the differential pressure across the member containing the orifice deforms the member to reduce the cross-sectional area of the orifice.

In another preferred embodiment of the invention particularly useful in medical applications where the non-gaseous fluids are liquid body fluids, the flow restriction means reduces the gas flow through the system by reducing the cross-sectional area available for flow through the orifice in the flow restricting means to from about 1 to about 75% of the cross-sectional area of the vacuum line.

In an additional preferred embodiment of the invention, the flow restriction means includes a plurality of orifices, with a closure member adjacent at least one orifice and disposed to close the orifice upon an increase in differential pressure across the closure member.

Another preferred embodiment of the invention includes a single orifice with a closure member disposed to partially close the orifice upon an increase in differential pressure across the closure member.

An additional preferred embodiment of the invention particularly useful in embodiments having the restriction means positioned outside the collection vessel includes a plurality of orifices which may have substantial differences in cross-sectional area. The orifices provide flow paths through the restriction means which contains chambers formed by a diaphragm. The differences in cross-sectional areas of the orifices can be mathmatically and empirically selected to provide optimum time and vacuum level response of the system. The selected cross-sectional areas create a differential pressure sufficient to deform the diaphragm to reduce the flow through the restriction means.

It is also preferred that the vacuum line have a diameter equal to or greater than that of the inlet conduit.

BRIEF DESCRIPTION OF DRAWINGS

The invention consists of the parts, constructions, arrangements, combinations and improvements shown and described. The accompanying drawings, which are incorporated in and constitute a part of this specification, illustrate several embodiments of the invention and, together with the description, serve to explain the principles of the invention.

Of the drawings.

DETAILED DESCRIPTION OF THE INVENTION

Reference will now be made to the present preferred embodiments of the invention, examples of which are illustrated in the accompanying drawings.

Figure 1:
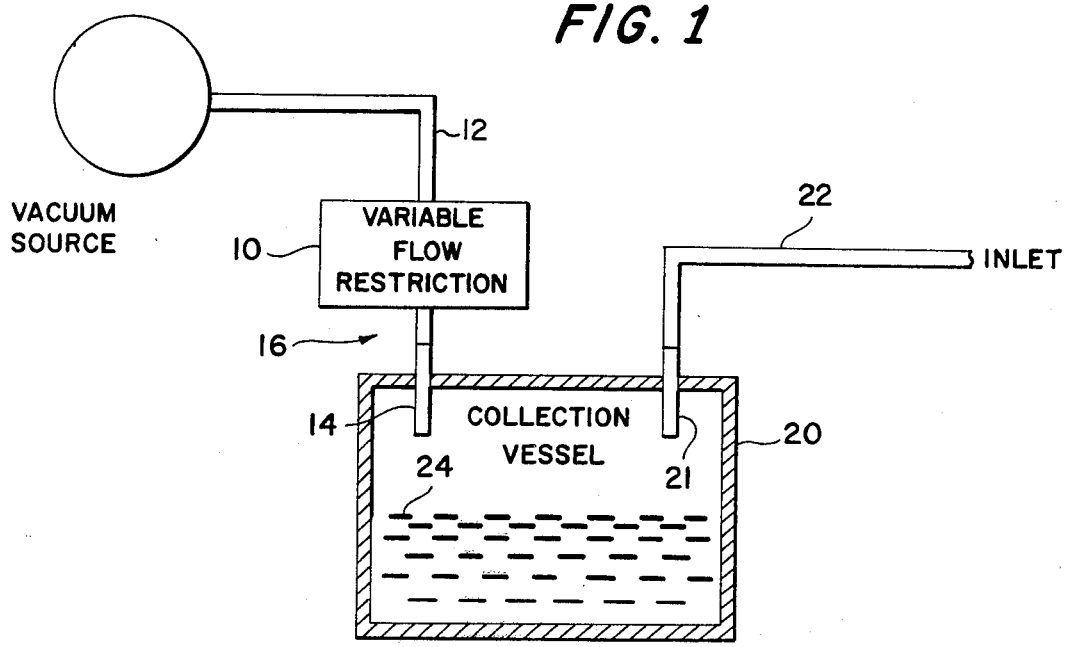
FIG. 1 is a schematic view of the present invention.

Referring now to FIG. 1, the collection system generally consists of a vacuum source connected to a closed collection vessel 20. The connection between the vacuum source and the collection vessel 20 is made through an outlet port 14, a vacuum conduit 12 and a variable flow restriction means 10. The outlet port 14 and the vacuum conduit 12 comprise a vacuum line 16. The flow restriction 10 is disposed to reduce the cross-sectional area of the vacuum line 16 in response to an increase in differential pressure across the flow restriction. While FIG. 1 shows the variable flow restriction 10 between the vacuum source and the outlet port 14, the variable flow restriction can be placed anywhere in the vacuum line 16 and still yield the improvements of the present invention. For example, the embodiments of FIGS. 2-10 have the variable flow restriction at the outlet port 14.

It is the function of the variable flow restriction 10 to reduce gas flow through the vacuum line 16 in response to increasing differential pressure across the flow restriction. Any significant reduction in the gas flow through the vacuum line 16 will improve the energy efficiency of the system. A preferred embodiment of the present invention would, at one point in the vacuum line, reduce the effective diameter of the vacuum line from 1 to 75%.

The reduction of the cross-sectional area available for flow and hence the gas flow through the vacuum line 16 reduces the rate of negative pressure build-up in the collection vessel 20 when the inlet conduit 22 is exposed to fluid materials. When the gas flow is restricted, the present invention can provide a rate of negative pressure build-up within the collection vessel 20 which is desirable to avoid tissue grab in medical applications, while stil providing satisfactory fluid flow rates within the inlet conduit 22. For all applications energy savings are achieved in operating the vacuum source, if the inlet conduit 22 is periodically exposed to the atmosphere.

The present invention provides a means of changing the flow restriction in response to conditions within the collection system. The advantage of the present invention is that in response to system conditions, the gas flow can be restricted to yield further benefits depending on collection conditions. For example, when the inlet 22 is exposed to the atmosphere, the vacuum within the collection vessel 20 is reduced by the ingestion of large quantities of gas into the collection vessel. The variable flow restriction means responds to the relatively large gas flow and resultant pressure differential across the variable flow restriction 10 by restricting the cross-sectional area of the vacuum line and hence the gas flow therein. This provides savings in energy by removing the necessity of pumping large quantities of gas through the pump section of the vacuum source. When the inlet 22 is exposed to a non-gaseous fluid, the vacuum increases within the collection vessel 20 and equalizes the pressure across the variable flow restriction 10 to a degree that the responsive element in the variable flow restriction does not further restrict gas flow therethrough.

In the manner described above, the rate of vacuum build-up within the collection vessel 20 can be more carefully controlled using a pressure responsive flow restriction means than is possible where a constant flow restriction is used.

For medical applications in which the volume of the collection vessel is typically about 2 liters and the vacuum line has an internal diameter of about ¼ to ½ inch, and the flow restriction means preferably has an effective restrictive position diameter of about 5% to 25% of the diameter of the vacuum line. This effective diameter corresponds to the effective diameter of the flow restriction means when the outlet port is exposed to atmospheric pressure.

Inlet conduit 22 is connected to the closed collection vessel 20 by means of inlet port 21. The fluid material to be collected 24 passes through the inlet conduit and inlet port into collection vessel 20.

The non-gaseous fluid material passing through the inlet port 21 is retrained in the collection vessel 20. The present invention is disclosed in FIG. 1 with a simple collection vessel. However, the invention is operable with any compatible means of collecting a non-gaseous fluid. Operable collection vessels would retain any non-gaseous fluids introduced through the inlet port 21 while preventing the non-gaseous fluids from being introduced to the outlet port 14 and the associated vacuum source. The size of the collection vessel affects the pressure response of a variable flow restriction means within the system. The pressure within a large collection vessel reacts slowly to changing pressure conditions at the inlet 22. When the collection vessel is small, its internal pressure changes quickly in response to the conditions at the inlet. Since the variable flow restriction responds to the pressure difference between the vacuum line and the collection vessel then a restriction will respond at different rates depending upon the size of the collection vessel.

A flow restriction of a given restrictive position effective diameter will cause a faster rate of vacuum build up with a small volume container than with a larger volume container. In general, in medical applications such as surgical site drainage systems, the volume of the collection vessel and the inlet conduit should be equal to or preferably greater than the volume of that portion of the vacuum line 16 extending between the flow restriction and the vacuum source. When the ratio of volumes is as described above, the variable flow restriction means can effectively slow down the rate of vacuum build-up in the container and inlet conduit. If the inlet conduit becomes blocked or partially blocked to gas flow, the slowing down of the rate of vacuum build-up desirably prevents tissue grabbing when the end of the inlet conduit is adjacent human tissue during suctioning.

From the foregoing discussion, it can be appreciated that the selection of the volume of the collection vessel and the variation of the effective diameter of the opening in the variable flow restriction means are interrelated parameters which are determined by the desired rate of increase of negative pressure and the energy savings desired.

An example of a suitable collection vessel for medical uses is taught in U.S. Pat. No. 3,863,663. Such a collection vessel has a volume of about 2 liters.

The collection system will, of course, ingest all liquids, gases and free flowing solid particles at the inlet 22 due to the differential pressure generated at the inlet 22 by the vacuum source. The system passes a gaseous fluid from the inlet to the vacuum source with no collection of such a gaseous fluid. A non-gaseous fluid 24 is retained in the collection vessel 20. The present invention is operable with liquid, foam or free flowing solid particles acting as fluids having sufficiently low viscosity to be transported through the inlet conduit.

The present invention is described in terms of medical apparatus and will be applicable in that use for the collection of liquid body fluids. The invention would also be operable with other non-gaseous fluids and need not be confined solely to medical applications.

Figure 2:
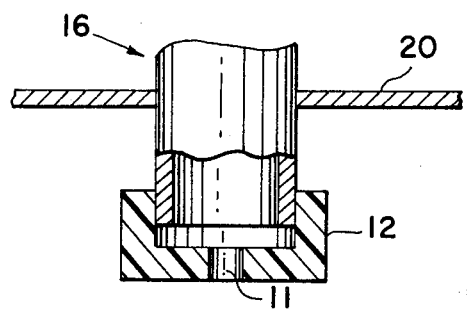
FIG. 2 is a partial cross section of one embodiment of the variable flow restriction means where an orifice in an elastically deformable member comprises the restriction.
Figure 3:
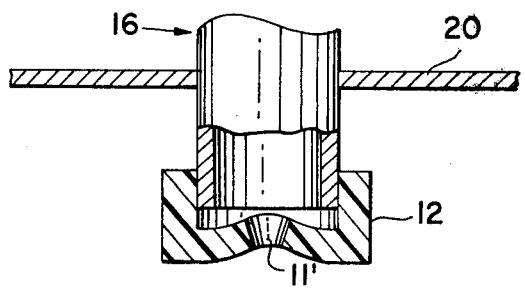
FIG. 3 is the embodiment of FIG. 2 where sufficient differential pressure has deformed the orifice reducing its cross-sectional area.

FIGS. 2 and 3 illustrate one embodiment of the present invention where the flow restriction means is an elastically deformable body 12 that includes an orifice 11. The orifice 11' as shown in FIG. 3 is reduced in cross-sectional area by elastic deformation of the body 12 in response to increasing differential pressure across the deformable body 12. FIG. 2 shows the configuration of the restriction when there is a relatively small differential pressure across the body 12 and the orifice 11 is in its undeformed state. The orifice in this configuration allows a rapid vacuum build-up within the collection vessel to ingest non-gaseous fluid material through the inlet 22. FIG. 3 shows the embodiment of FIG. 2 where the orifice 11' is deformed to reduce its cross-sectional area, therefore reducing the rate of gas flow through the flow restriction means. The body 12 is deformed as the result of increased differential pressure across the body 12 resulting from the exposure of the inlet 22 to the atmosphere. The ingestion of gaseous fluids into the collection vessel increases the pressure within the collection vessel while the downstream side of the body 12 is exposed to lower pressures. This increased differential pressure is responsible for the deformation of the elastic body 12.

The shape of the orifice 11 through the body 12 is not known to be critical. It is preferred that the shape be oval, but round or irregular shapes are operable with this invention so long as the orifice is not completely closed by deformation of the member 12. Preferably the embodiment disclosed in FIGS. 2 and 3 would have an orifice effective restrictive position diameter of from 1 to 75% of the diameter of the vacuum line. The elastically deformable body 12 has an orifice shape and size, material modulus and wall thickness appropriately matched to the vacuum level produced by the vacuum source to present a variable orifice that is reduced in cross-section flow area from the vacuum line. Preferably, the elastically deformable body should not be so elastic that the cross-sectional area of the orifice therethrough would, after passing through a minimum value, re-expand upon further deformation of the body 12. If such a configuration has that characteristic, it can be alleviated by providing some means of backing up the deformable body 12 at the maximum desired deflection of the deformable body. This back up means could additionally further restrict the flow area of the orifice in the deformed position.

While the disclosure describes the restriction in terms of percentages of diameter and thus cross-sectional areas, one skilled in the art can devise flow restrictions and orifice configurations of various shapes. The use of various orifice shapes and configurations are equivalent to the percentage changes in diameter that are disclosed if they have the same effect on flow within the vacuum line. The flow effect of various orifice configurations can be obtained from experimental measurements on actual systems, and in some situations can be calculated from existing empirical data using well know relationships.

Figure 4:
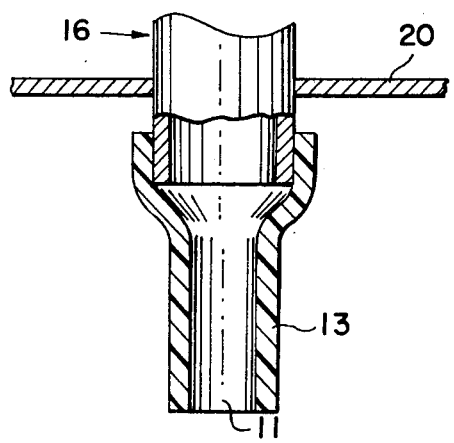
FIG. 4 is a partial cross section of another deformable member comprising the flow restriction means in its undeformed state.
Figure 5:
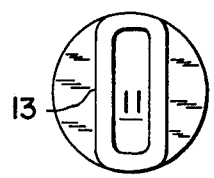
FIG. 5 is an end view of the embodiment of FIG. 4.
Figure 6:
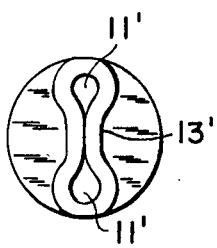
FIG. 6 is the end view of embodiment of FIGS. 4 and 5 now deformed in response to increased differential pressure.
Figure 7:
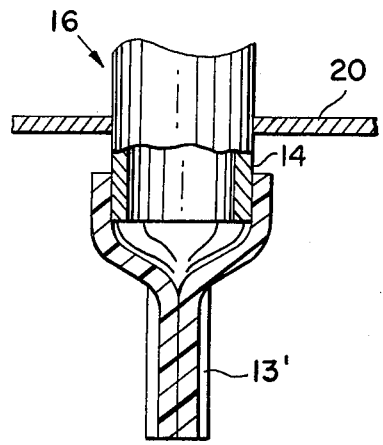
FIG. 7 is a partial cross section of the embodiment of FIGS. 4, 5 and 6 showing the change in configuration due to the increase in differential pressure.

FIGS. 4–7 disclose and additional embodiment of the invention where the flow restricting means in the vacuum line 16 is a deformable body 13. However, this deformable body reduces the cross-section of the orifice 11 in a manner dissimilar from the embodiment disclosed in FIGS. 2 and 3. FIG. 4 is a cross-sectional view of an elastic member 13 generally tubular in configuration, but preferably having a flattened end portion. When the pressure differential across the orifice 11 is sufficiently low, the member 13 remains open providing the minimum value of flow restriction in the system. The configuration of the orifice is shown by an end view of the embodiment of FIG. 4 in FIG. 5. Upon an increase in the differential pressure across the deformable body 13, the pressure collapses the walls of the member 13 to reduce the cross-sectional area of the orifice therethrough. FIGS. 6 and 7 illustrate the configuration of the collapsed member 13′. In FIG. 6, the orifices 11′ remain open through the member 13′ allowing gas flow therethrough so as not to completely close off the vacuum source from the collection vessel 20. FIG. 7 is a partial cross section of the member 13′ in its collapsed state showing the sealing of the central portion of the member 13′ in response to the differential pressure applied thereto.

As with the elastically deformable body 12 disclosed in FIGS. 2 and 3, the thickness and configuration of the member 13 can be readily determined for different materials of construction by actual trial.

Figure 8:
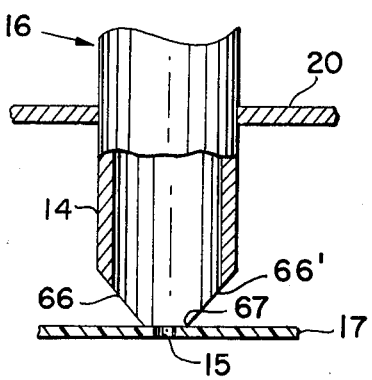
FIG. 8 is a cross-sectional view of another embodiment of a pressure responsive flow restriction means.

FIG. 8 discloses a flow restriction means having a plurality of openings. A first opening, orifice 15, in closure member 17 preferably has a constant cross-sectional area. The flow restriction means as here embodied includes two additional openings, 66 and 66′ in outlet port 14, with closure member 17 attached to outlet port 14 adjacent the openings 66 and 66′. Closure member 17 is responsive to increases in differential pressure across the closure member. The closure member 17 obstructs the openings 66 and 66′ as differential pressure across the closure member 17 increases. The closure member 17 is preferably constructed of an elastomeric material of low modulus and is mechanically affixed at point 67 to a rigid outlet port 14 of the vacuum line 16. As illustrated in FIG. 8, outlet port 14 is beveled to form a plurality of triangular openings 66 and 66′, and a deformable flexible closure member 17 is attached to the beveled extremity with the closure member 17 having an orifice 15 therein in flow communication with the opening area. Flexible closure member 17 includes flexible marginal portions disposed to close the triangular openings 66 and 66′ upon an increase in differential pressure across the closure member 17.

Figure 9:
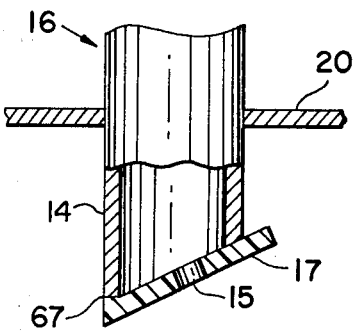
FIG. 9 with the closure member shown in the restrictive flow position is a cross-sectional view of still another embodiment of a pressure responsive flow restriction means.

FIG. 9 illustrates an additional embodiment of the flow restriction means in which a deformable closure member 17 shown in the restrictive flow position is attached to one end portion of the outlet port 14 at 67 with the closure member 17 partially obstructing the outlet port upon the application of maximum differential pressure across the closure member 17. At less than maximum pressure differentials closure member 17 would not seal around the periphery of outlet port 14. The partial obstruction allows the passage of gas through the collection system to the vacuum source. In the embodiment of the FIG. 9, the means used to accomplish the incomplete sealing is an orifice 15 through the closure member 17. There are means of accomplishing the incomplete sealing other than an orifice through the closure member as shown in FIG. 9. The sealing surface of the tube 14 could have indentations therein to allow passage of gas through the tube 14 even upon closure of the opening by the member 17. The member 17 could have indentations on its sealing surface disposed to allow the passage of gas therethrough, even upon complete deflection of the member 17.

Figure 10:
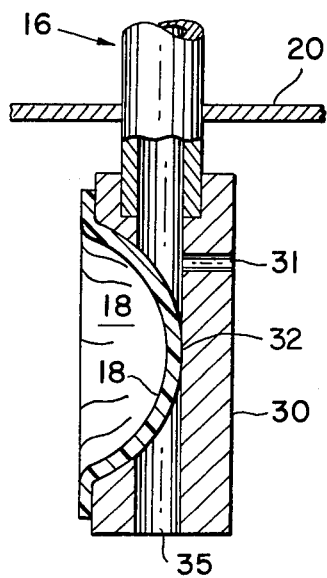
FIG. 10. is a cross-sectional view of a pressure responsive flow restriction means utilizing a deformable diaphragm.

FIG. 10 is a cross section of another preferred embodiment of the present invention where the deformable member for reducing gas flow through the vacuum line 16 by changing the cross-sectional area is a deformable diaphragm 18. In this embodiment, a housing 30 has a conduit 35 passing through the housing. The conduit can be reduced in cross section by a deformable diaphragm 18 adjacent the conduit and capable of being deformed into the conduit. One surface of the diaphragm is exposed to an upstream source of pressure, here the collection vessel pressure. The second surface of the diaphragm is exposed to the pressure within the conduit 35. There is a by-pass means within the housing 30 to pass gas through the housing 30 even at maximum deflection of the diaphragm 18. In FIG. 10, the by-pass for the flow of gas through the housing 30 at maximum deflection of the diaphragm 18 is an additional conduit 31 in the housing 30. The conduit 31 is significantly smaller in diameter than conduit 35 and communicates with the vacuum line 16 at a position between the diaphragm 18 and the vacuum source. In this embodiment, the diaphragm is shown at maximum deflection sealing the conduit 35 at its mating surface 32. The embodiment of FIG. 10 preferably utilizes a circular diaphragm 18 and a spherical seat within the housing 30 comprising the mating surface 32. Such a configuration provides for the full deflection of the diaphragm 18 without inducing wrinkles therein that may unpredictably effect gas flow past the sealing surface 32.

Figure 11:
FIG. 11 is a cross-sectional view of a diaphragm having indentations on its mating surface.

FIG. 11 is a cross section of a diaphragm 18′ having indentations 19 therein comprising a by-pass means. The embodiment of FIG. 11 which obviates the need for conduit 31 allows gas to pass through the housing at full diaphragm deflection by providing indentations 19 at the mating surface 32 where the deflected diaphragm and the housing meet. An alternative method of providing similar means of allowing gas to pass through the housing at full diaphragm deflection are indentations in the mating surface 32 of the housing 30.

The embodiments of the invention disclosed in FIGS. 2–10 have all placed the flow restriction 10 within the collection vessel 20 at the termination of the vacuum line 16. This configuration is presently preferred but the variable flow restriction 10 need not be placed within the collection vessel 20.

Figure 12:
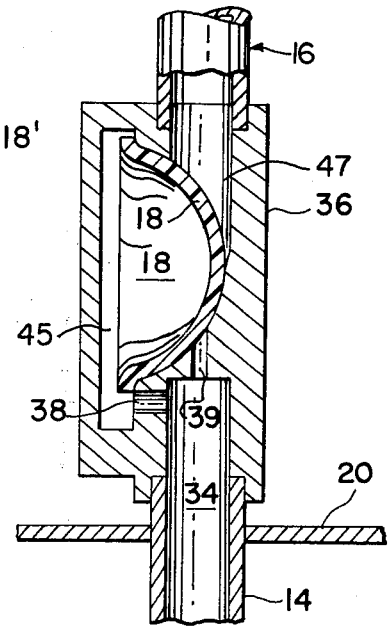
FIG. 12 is a cross-sectional view of a pressure responsive flow restriction means utilizing a deformable diaphragm and internal orifices to deflect the diaphragm.
Figure 13:
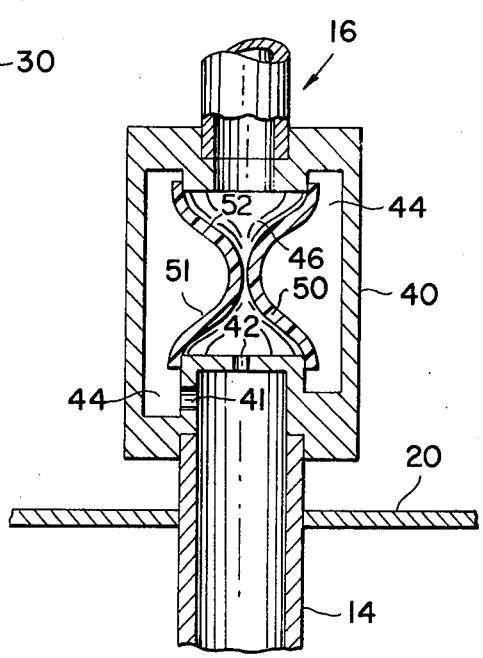
FIG. 13 is a cross-sectional view of a pressure responsive flow restriction means using a tubular diaphragm and internal orifices to deflect the diaphragm.

FIGS. 12 and 13 disclose two further embodiments where the flow restriction means is placed outside the fluid collection vessel 20, and the differential pressure that varies the flow restriction is determined by the relative size of orifices within a housing containing a deformable closure member.

FIG. 12 discloses a flow restriction means consisting of a housing 36 in flow communication with the vacuum line 16, with the housing 36 having a deformable diaphragm 18 mounted on the interior of the housing 36 for dividing the housing 36 into two chambers 45 and 47. A first orifice 38 in the housing 36 permits flow communication between the collection vessel 20 and the chamber 45. A second orifice 39 in the housing 36 is in flow communication with the collection vessel 20 and the second chamber 47. The second orifice 39 has a diameter significantly less than inlet 34 of the restriction means to reduce the effective cross sectional area available for flow through the second chamber 47 upon an increase in differential pressure across the diaphragm 18. The embodiment of FIG. 12 has means (not shown) within the housing 36 for maintaining a significantly reduced gas flow through the housing 36 at the full deflection of the diaphragm 18. The means used to maintain a reduced gas flow through the housing 36 upon full deflection of the diaphragm 18 may be a roughened surface at the point where the diaphragm and the housing contact each other, indentations on the contact surface in the housing 36 or indentations on the contact surface of the diaphragm 18. The different cross-sectional areas of orifice 39 and inlet 34 creates a differential pressure across the diaphragm that deforms the diaphragm in response to pressure changes in the vacuum system. In a further preferred embodiment of the embodiment of FIG. 12, the diaphragm would incompletely seal against its mating surface to reduce the cross section of the second chamber 47.

FIG. 13 illustrates an embodiment of the invention where the flow restricting means is a housing 40 having a tubular diaphragm 50 therein. The diaphragm has one surface 51 exposed to a chamber 44 in flow communication through a first orifice 41 with the collection vessel 20. The opposite surface 52 of the diaphragm 50 is exposed to a chamber 46 in flow communication with the vacuum source and through an orifice 42 in flow communication with the closed collection vessel 20. The size of the orifice 42 is significantly smaller than that of the inlet 14 diameter, thereby creating sufficient differential pressure across the diaphragm 50 to deform the diaphragm 50 sufficiently to reduce the cross-sectional area of the second chamber 46. In this embodiment, the action of the differential pressures on the diaphragm 50 tends to flatten the diaphragm to reduce the cross-sectional area available for flow from the collection vessel 20 to the vacuum line. The restriction means can readily be provided with means to insure that gas passes through the restriction even at maximum diaphragm deflection.

The specific means of insuring gas flow through this embodiment of a restriction means could be the indentations shown in FIG. 11 on the internal surface 52 of the diaphragm 50 of this embodiment, or there could be an orifice similar to that of orifice 31 in FIG. 10 downstream from the diaphragm 50 and significantly smaller in diameter than orifices 42 and 41 thereby effectively by-passing the flow restriction created by the deformation of the diaphragm 50.

The placement of the variable flow restriction means 10 outside the collection vessel 20 has the advantage of permitting access to the flow restriction means without disturbing the interior of the collection vessel. A further advantage is that if a present system not incorporating a variable flow restriction is desired to be improved with the present invention, the variable flow restriction can be added at a portion of the vacuum line 16 convenient to the present system without excessive modifications of the configuration of the prior device.

The present invention has been described in terms of preferred embodiments, and it should be apparent to those skilled in the art that various modifications and variations can be made in the invention without departing from the scope of the invention as defined by the appended claims.

What is claimed is:

1. A system for collecting body fluids comprising:
   (a) a vacuum source;
   (b) a closed fluid collection vessel having an inlet port and an outlet port, said ports being in flow communication above the level of fluid within said vessel;
   (c) an inlet conduit having its discharge end in flow communication with said inlet port and its intake end disposed to be immersed in said body fluid;
   (d) a vacuum conduit connecting said vacuum source and said outlet port; and
   (e) pressure responsive means associated with said vacuum conduit for reducing air flow to said vacuum source in response to a significant increase in pressure within said collection vessel caused by said inlet conduit ingesting significant amounts of air.

2. The system of claim 1 wherein said pressure responsive means has a restrictive position and a non-restrictive position and has an effective diameter in the restrictive position available for flow of from 1 to 75% of the effective diameter of the vacuum line.

3. The system of claim 2, wherein said pressure responsive means is an elastically deformable body that includes an orifice, the area of said orifice being reduced in cross-section by elastic deformation of said body in response to increasing differential pressure across said deformable body caused by said intake end of said inlet conduit ingesting significant amounts of air.

4. The system of claim 1, wherein said pressure responsive means comprises a member having a first opening and a second opening, each opening in flow communication with said collection vessel and said vacuum source, and a closure member positioned adjacent said second opening for obstructing said second opening in response to an increase in differential pressure across said closure member.

5. The system of claim 4, wherein said pressure responsive means comprises a tube having one extremity beveled to form a plurality of discreet openings, a deformable, resilient closure member attached to said beveled extremity, said closure member having an orifice therein in flow communication with said discreet openings, and including flexible marginal portions disposed to close said discreet openings upon an increase in differential pressure across said closure member.

6. The system of claim 2, wherein the pressure responsive means comprises a tube having a deformable closure member attached thereto, said closure member positioned to partially obstruct one of said openings in response to the application of increasing differential pressure across said closure member.

7. The system of claim 1, wherein the pressure responsive means comprises a housing having a conduit, a deformable diaphragm positioned adjacent said conduit for reducing the cross section of said conduit, one surface of said diaphragm being exposed to the interior of said collection vessel, and a second surface of said diaphragm being exposed to the pressure in said conduit, and by-pass means in said housing disposed to pass gas through said housing to said vacuum source even at maximum deflection of said diaphragm.

8. The system of claim 7, wherein the by-pass means comprise indentations in the surface of said housing where said diaphragm and said housing contact when said diaphragm is fully deflected.

9. The system of claim 7, wherein the by-pass means is a second conduit that communicates with said vacuum line at a point between said diaphragm and said vacuum source.

10. The system of claim 2, wherein said flow restriction means comprises a housing in flow communication with said vacuum line, a deformable diaphragm mounted on the interior walls of said housing for dividing said housing into two chambers, a first orifice in said housing permitting flow communication between said collection vessel and one of said chambers, a second orifice in said housing in flow communication with said collection vessel and the second of said chambers, said second orifice having a diameter significantly less than the inlet diameter of the flow restriction means to permit reducing the effective cross section for flow through said second chamber upon an increase in differential pressure across said diaphragm.

11. The system of claim 10, wherein said diaphragm incompletely seals against its mating surface too reduce the cross-sectional area of said second chamber.

12. The system of claim 10, wherein the flow restriction means consists of a housing having a tubular diaphragm therein and the first orifice communicates with the exterior of said diaphragm and said second orifice communicates with the interior of said tubular diaphragm.

13. The system of claim 1, wherein the volume of said collection vessel and said inlet conduit are at least equal to the volume of the portion of said vacuum line between said flow restriction means and said vacuum source.

* * * * *